(12) United States Patent
Zink et al.

(10) Patent No.: US 6,521,443 B1
(45) Date of Patent: Feb. 18, 2003

(54) GROWTH MEDIUM FOR LACTOBACILLI CONTAINING AMINO ACIDS, NUCLEOSIDES AND IRON

(75) Inventors: Ralf Zink, Le Mont Pelerin (CH); Marina Elli, Lausanne (CH); Roberto Reniero, Le Mont Pelerin (CH); Lorenzo Morelli, Piacenca (IT)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/559,355

(22) Filed: Apr. 27, 2000

(30) Foreign Application Priority Data

Apr. 30, 1999 (EP) .............................. 99108717

(51) Int. Cl.$^7$ .............................. A23C 9/12; C12N 1/00; C12N 1/20
(52) U.S. Cl. ................... 435/253.6; 426/34; 435/252.9; 435/853
(58) Field of Search .............................. 424/93.45, 1.73, 424/169; 435/243, 252.9, 253.6, 853; 426/34

(56) References Cited

U.S. PATENT DOCUMENTS

| | | | |
|---|---|---|---|
| 3,480,443 A | 11/1969 | Schuler | 99/59 |
| 4,463,095 A | 7/1984 | Emi et al. | 435/190 |
| 4,544,559 A | * 10/1985 | Gil et al. | 426/72 |
| 4,879,238 A | 11/1989 | Hata | 435/244 |
| 4,888,292 A | 12/1989 | Hata | 435/244 |

FOREIGN PATENT DOCUMENTS

| | | |
|---|---|---|
| DE | 27 23 191 | 12/1977 |
| DE | 32 44 129 | 11/1983 |

OTHER PUBLICATIONS

Patent Abstracts of Japan, vol. 014, No. 280 (C–0729), Jun. 18, 1990 & JP 02 086769 A(Kubota Ltd), Mar. 27, 1990.
Patent Abstracts of Japan, Vol. 018, No. 367 (C–1223), Jul. 11, 1994 & JP 06 098760 A (Snow Brand Milk Prod. Co. Ltd.), Apr. 12, 1994.

* cited by examiner

*Primary Examiner*—David M. Naff
*Assistant Examiner*—Deborah K. Ware
(74) *Attorney, Agent, or Firm*—Winston & Strawn

(57) ABSTRACT

A growth medium adapted for the growth of a variety of different lactobacilli is provided. The medium is based on milk which is supplemented by at least four free amino acids, at least two ribonucleosides or other ribonulcleotide precursors, and iron. A variety of different Lactobacilli, particularly Lactobacilli belonging to Johnson's group A and B groups, are able to reproduce at rates approximately the same as milk supplemented with yeast extract. This medium when used in the production of dairy products that contain Lactobacilli does not contain the off-flavor of a fermented medium that had been supplemented with yeast extract.

16 Claims, 2 Drawing Sheets

GROWTH MEDIUM FOR LACTOBACILLI CONTAINING AMINO ACIDS, NUCLEOSIDES AND IRON

FIELD OF THE INVENTION

The present invention pertains to a novel medium adapted for the growth of Lactobacilli, which comprises a milk-derived base supplemented by at least four amino acids, ribonucleotide precursors, and iron. In particular, the present invention relates to the use of said novel medium for cultivating a variety of different Lactobacillus strains, e.g. *L. johnsonii, L. acidophilus, L. gallinarum*, etc. for the preparation of dairy products.

BACKGROUND OF THE INVENTION

Lactic acid bacteria have been used since long for the production of a variety of food material, such as yoghurt, cheese, curd etc. In addition to their general usage in the food industry for fermentation purposes quite recently some strains belonging to the genus Lactobacillus or Bifidobacteria have attracted a great deal of attention due to probiotic properties attributed to them. Consequently, there was a desire to improve cultivation conditions so as to be able to maximize the growth and output of the microbial biomass.

One difficulty with large scale cultivation and application of lactic acid bacteria is their different nutritional requirements. In this context, different strains belonging to one specific genus or species require different media for optimal growth, which makes a standardized production of microbial biomasses complicated and cumbersome. For example, in producing a biomass of different strains of the genus Lactobacillus, a variety of different media have to be utilized, each of which does, however, only fulfil the nutritional needs of one particular strain, while not providing proper nutrients and/or environment for sufficient growth of other Lactobacillus strains therein.

A medium often utilized for cultivating lactic acid bacterial strains is cow milk. On the one hand, this medium provides a complex natural environment and its fermentation products, e.g. yoghurt, may be directly used as food material. Yet, this medium has proved to only support the growth of a limited number of strains of lactic acid bacteria. For example, Lactobacilli of the Johnson's group A and B have been demonstrated to be essentially unable to proliferate and grow in milk, which makes this medium useless for said strains.

In some cases, bacterial growth could be improved when substances of an undefined and very complex composition, such as yeast extract or peptones of various origins, are added to the milk. However, these additional components can often cause an off-flavor with the result that cultures growing in a medium supplemented in such a way may not be used for industrial manufacture of dairy products. Moreover, the costs involved and the sometimes varying results in repeatability of achievable bacterial counts, makes such a process unsuitable for a commercial manufacture of these microbial strains.

In view of this, a problem of the present invention is to provide a medium which supports the growth of Lactobacillus strains while avoiding the shortcomings of the art.

SUMMARY OF THE INVENTION

The present invention solves the shortcomings of the art by providing a medium for the growth of Lactobacillus strains. The medium comprises a milk-derived base that has been supplemented by an additive system that includes at least four amino acids, at least two ribonucleosides or other ribonucleotide precursors, and beneficially iron. These components are added in amounts sufficient in combination to promote growth of lactobacilli in the medium. The specific amount of each of the ribonucleotide precursors, i.e., free bases, ribonucleosides, and deoxyribonucleosides, to be added to the base lie in the range from about 10 to about 500 milligrams per liter (mg/l) base, preferably from about 10 to about 100 mg/l base. Preferably, iron is added to the base in an amount ranging from about 10 to about 200 mg/l and more preferably in an amount from about 50 to about 100 mg/l milk.

Advantageously, the base is supplemented by at least four amino acids. The amino acids may be selected from any known or existing amino acid available to the skilled person. The amount of amino acids to be added to the milk base lies in the range of from about 10 to about 200 mg/l, preferably from about 50 to about 100 mg/l milk. In a preferred embodiment, the amino acids to be used are selected from the group consisting of cysteine, alanine, serine and isoleucine, which are found to particularly improve the growth conditions for Lactobacilli.

According to yet another preferred embodiment the base may also be supplemented by compounds providing antioxidant or reducing activity. Examples of such compounds include ascorbic acid, vitamin E, tocotrienol, ubiquinol, 13-carotene and other carotinoids, rosemary compounds (e.g. camosol) and other flavonoids, and other sulphur containing antioxidants including glutathione, lipoic acids, N-acetylcysteine or compounds bearing suithydryl groups, cysteine or thioglycollic acid, or mixtures thereof. Cysteine is preferred as an amino acid and as a compound providing reducing activity.

DETAILED DESCRIPTION OF THE INVENTION

During the extensive studies leading to the present invention it has been found that various parameters seem to be responsible for the growth of Lactobacilli in a milk-based medium.

The milk-derived base to be included in the medium may be milk in all of its variations, such as whole or partially de-fatted milk, skim milk or UHT milk, or may be prepared from dried milk powder by addition of water. The fluid milk base may be used as such or other well known components may be added, such as e.g. water, to dilute the milk to a desired degree.

Cow's milk is known to have a specific content of ribonucleotides, which varies depending on the season and country of production. The purine derivatives account for just small fraction, while about more than 95% of the ribonucleotides in milk is represented by orotic acid. This compound is used as a pyrimidine precursor by bacterial cells. The low content of adenine and guanine nucleosides in milk negatively affects the bacterial growth with the proviso of some strains that may perform a "de-novo" synthesis of DNA and RNA precursors, such as L. casei and L. plantarum. However, even inhibitory effects have been observed in some cases when adding purine derivatives to milk.

Some Lactobacillus strains, such as L. johnsonii, L. gasseri, L. crispatus, L. amylovorus, L. gallinarum and L. acidophilus, are unable to reproduce at high density in milk. A combination of different chemicals which were hypothesized to be capable of replacing growth stimulatory substances of undefined composition, i.e., yeast extract, was studied.

In order to find the identity of other stimulatory substances, several trials were performed with ribonucleotide precursors, that is free bases such as adenine, guanine, cytosine, thymine, and uracil, ribonucleosides such as adenosine, cytidine, uridine, and guanosine, and 2'-deoxyribonucleosides such as deoxyadenosine, deoxyguanosine, deoxycytidine, deoxyuridine and thymidine. These compounds were supplemented to milk as concentrated alkaline or neutral solutions at different concentrations.

An addition of ribonucleosides improved the growth conditions for Lactobacilli in milk, with adenosine and guanosine showing the strongest effect. This finding confirmed the hypothesis that the low level of purines in milk negatively affects bacterial growth therein. Generally it was found that the high content of orotic acid represents a stimulatory factor for Lactobacillus growth. Without being bound by theory, it is believed that the high content of orotic acid allows the synthesis of pyrimidine bases. No significant differences in pH-values were detected by the addition of free bases and deoxyribonucleosides between aerobic and anaerobic conditions. More than 1 log improvement in bacterial growth was observed in bases supplemented by ribonucleosides. The positive effect was observed particularly with the addition of ribonucleosides in anaerobic environment.

Figure 1:
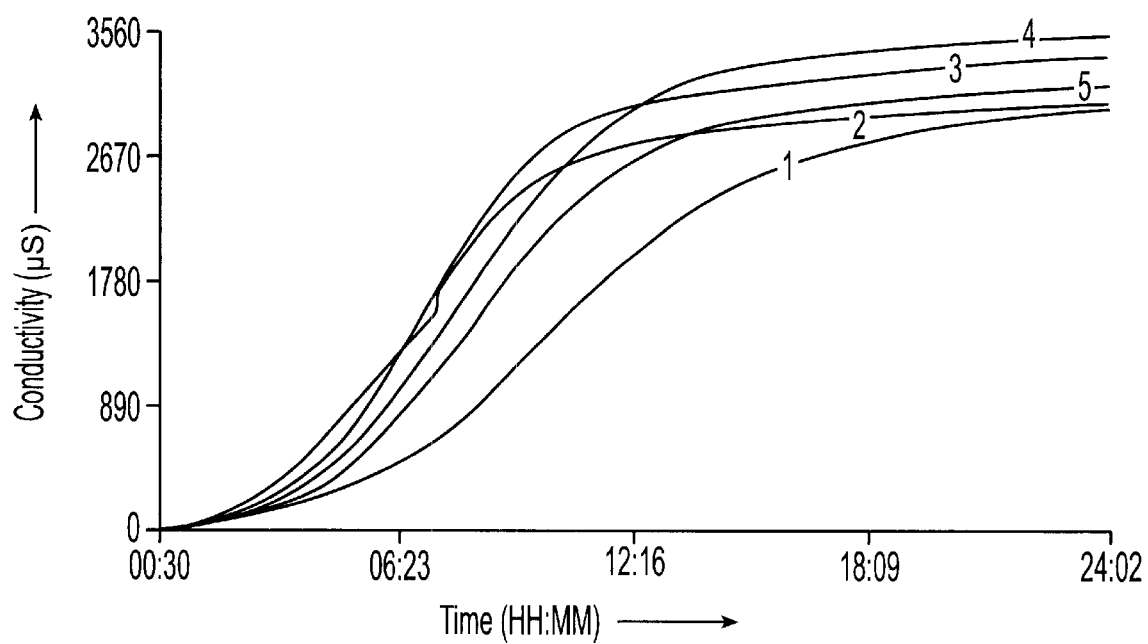
FIG. 1 shows a comparison between RABIT curves obtained during 24 hours incubation for *L. johnsonii* Lal (NCC 533) in 10% skim and whole fat ultra-high temperature pasteurized (UHT) milk supplemented with 1% yeast extract versus a mixture of four ribonucleosides, four amino acids and ferrous sulphate as follows; (1) contained whole UHT milk, four ribonucleosides, and four amino acids; (2) contained whole fat UHT milk and yeast extract; (3) contained skim milk and yeast extract; (4) contained skim milk, four ribonucleosides, four amino acids, and ferrous sulphate; and (5) contained skim milk, adenosine and guanosine, four amino acids, and ferrous sulphate.
Figure 2:
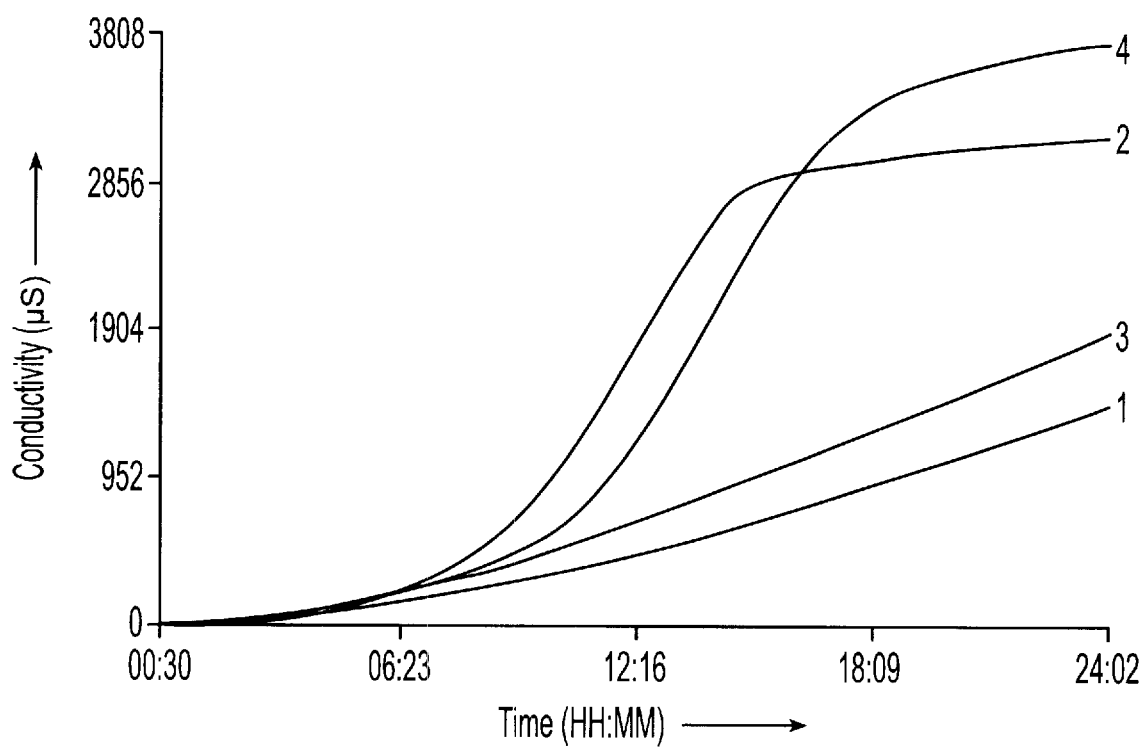
FIG. 2 shows a comparison between RABIT curves obtained during 24 hours incubation which demonstrates the effect of supplementing of a 10% skim and whole fat UHT milk with four ribonucleosides, four amino acids and ferrous sulphate on the growth of *L. gallinarum* DSM 33199$^T$ as follows; (1) contained 10% skim milk; (2) contained 10% skim milk, four amino acids, four ribonucleosides, and ferrous sulphate; (3) contained whole fat UHT milk; and (4) contained whole fat UHT milk, four amino acids, four ribonucleosides, and ferrous sulphate.

The best improvements for increasing the number of Lactobacilli by addition of ribonucleosides and the strongest acidification levels, respectively, were achieved by the addition of adenosine, guanosine, and/or cytidine and uridine in an amount of about 0.1 grams per liter each. This mixture supported L. johnsonii, L. acidophilus, and L. gallinarum growth at levels comparable to those achieved by the addition of yeast extract (see FIGS. 1, 2 and Table 3). However, no comparable positive effects were observed with other Lactobacillus strains, for example from the species L. amylovorus, L. crispatus and L. gasseri.

Addition of free bases, i.e., adenine, cytosine, uracil, thymine and guanine, to milk in place of ribonucleosides as supplements provided similar results, particularly if magnesium and aspartic acid were also added. In addition, several trials were conducted by supplementing milk with different 2'-de-oxynucleosides which brought about an increase of the viable cell number of merely some particular strains.

None of the mentioned chemical additives was able to support bacterial growth for a plurality of different bacterial strains at a high level if added alone to the milk. It has surprisingly been found that a combination consisting of amino acids, ribonucleotide precursors, and iron, e.g., in the form of iron sulphate, promotes the growth of a variety of different Lactobacillus species. Ribonucleosides are the preferred ribonucleotide precursors. In experiments, in which the number of the different compounds in the above combination mixture was reduced to a minimum it could be seen that the least number for each of the compounds specified to be added to the milk is at least two ribonucleosides, preferably adenosine and guanosine, four amino acids and iron. This mixture was able to improve growth of a variety of different Lactobacillus strains, such as those of the Johnson's group, with cell counts and a final pH comparable to that obtained by addition to the milk of yeast extract or peptones.

The addition of iron to the medium supplemented with a combination of the above chemicals was surprisingly found to improve the results obtained. Without being bound by theory, this discovery may be explained because, despite its rich composition, milk presents a strong deficiency in available iron, which in its natural state is complexed as lactoferrin and is therefore unavailable for any microorganism growing therein.

The best results were obtained by addition of adenosine, guanosine, and/or cytidine and uridine in an amount of 0.1 g/l each; alanine, serine, isoleucine, cysteine in an amount of 0.05 g/l each; and $FeSO_4$ in an amount of 0.1 g/l.

The fact that both skim and whole fat UHT milk gave good results when supplemented with the combination of the above compounds led to the hypothesis that the fatty components of milk had no role in stimulating Lactobacillus growth, and that sterilization treatments (UHT) did not negatively affect the potential of milk to support bacterial development.

EXAMPLES

The following examples illustrate the invention without limiting the same thereto.

Bacterial strains and culture were prepared as follows. L. Johnsonii strains ATCC $33200^T$, La1(NCC 533), ATCC 11506 (formerly known as L. acidophilus R-26), ATCC 332, DSM 20553, L. acidophilus ATCC $4356^T$, La1O (NCC 90), L. gasseri DSM $20243^T$, L. crispatus DSM $20531^T$, L. amylovorus $DSM20584^T$ and L. gallinarum DSM $33199^T$ were propagated in MRS (Difco) broth or agar at 37° C.

Skim milk (Difco) 10% w/v in sterile water and whole fat UHT milk (Parmalat, Italy) were used to perform the growth assays. The milk tubes were 1% inoculated from an overnight MRS culture washed twice and finally re-suspended with the same amount of sterile distilled water in order to avoid nutrient transfer via the medium.

Milk tubes were incubated aerobically in a thermostat (Sorvall Heraeus) at 37° C. for 24 hours, or anaerobically in an anaerobic incubator (Model 1024, Forma Scientific, USA) at 37° C. for 24 hours.

The chemicals supplemented to the milk were added as concentrated solutions prepared according to standard methods, i.e., the Merck Index instructions. The final pH of milk was adjusted to 6.8 after supplementation using an aqueous 4N sodium hydroxide solution. The initial pH of the 10% skim milk solution and whole fat UHT milk was 6.8 and 6.7, respectively.

The growth results were estimated by cell counts and a final pH measurement performed after 24 hours incubation at 37° C. Rapid Analysis of Bacterial Impedance Technique (RABIT) (Don Whitley Scientific, West Yorkshire, UK) was used to perform trials with skim and whole UHT milk for 24 hours at 37° C.

The experiments were performed using the listed 11 strains of all six species of the Johnson's group A and B, including the type strain of *L. johnsonii* ATCC 33200 and *L. johnsonii* Lal (NCC 533), in order to determine each species and strains' nutritional requirements in milk. The results led to the identification of some chemicals able to reproduce the positive effects of yeast extract and other substances of chemically undefined composition on bacterial growth in milk.

The strains under investigation were demonstrated not to be able to grow efficiently in either un-supplemented 10% skim or in un-supplemented whole fat UHT milk. The results, summarized in Table 1 for *L. johnsonii*, indicate that a moderate acidification of these natural media occurred over the 24 hours incubation, corresponding to less than a 1 log increase of final viable cell numbers even if the incubation was performed under anaerobic conditions. The same behavior in both skim and whole fat UHT milk was observed also for the type strains of *L. gasseri, L. amylovorus, L. crispatus, L. acidophilus* and *L. gallinarum*.

The supplementation of skim milk with 1% v/v yeast extract (Adsa, Italy) resulted in a 2 log improvement in the viable cell number. This result was confirmed using whole fat UHT milk. After 24 hours incubation a final pH of 4.0 was obtained with yeast extract addition. See Table 1 for the results. The final yeast extract concentration required for optimal bacterial growth varied between 0.1 and 1.0% v/v. The development of off-flavors and color changes were observed in fermented dairy products supplemented with this substance.

TABLE 1

|  | pH | CFU/ml | pH | CFU/ml |
|---|---|---|---|---|
|  | 10% skim milk | | 1% skim and yeast extract | |
| AEROBIOSIS | | | | |
| Initial Value | 6.8 | $1.0 \times 10^7$ | 6.8 | $1.0 \times 10^7$ |
| 24 hour value | 6.0 | $1.8 \times 10^7$ | 3.9 | $300 \times 10^7$ |
| ANAEROBIOSIS | | | | |
| Initial Value | 6.8 | $1.0 \times 10^7$ | 6.8 | $1.0 \times 10^7$ |
| 24 hour value | 5.9 | $7.0 \times 10^7$ | 3.8 | $320 \times 10^7$ |
|  | UHT milk | | UHT milk and yeast extract | |
| AEROBIOSIS | | | | |
| Initial Value | 6.7 | — | 6.7 | — |
| 24 hour value | 6.3 | — | 3.9 | — |

The final pH and cell counts were after 24 hours incubation of *L. johnsonii* La 1 (NCC 533) in 10% skim/UHT milk and after supplementation with 1% yeast extract. Similar results were shown for the other investigated *L. johnsonii* strains, with exception of strain ATCC 332, which did not show growth even with yeast extract addition. This data clearly showed the inability of UHT milk or of 10% skim milk to promote the growth of strains of *L. johnsonii* in the absence of yeast extract. As mentioned previously, however, yeast extract adversely affects the taste and other properties of the dairy product after fermentation.

A mixture of 19 amino acids (alanine, glycine, histidine, lysine, phenylalanine, proline, serine, threonine, cysteine, arginine. aspartic acid, asparagine, glutamic acid, isoleucine, leucine, methionine, tyrosine, tryptophane and valine) was added to skim milk (final concentration 0.05 g/l of each amino acid) producing a positive effect on *L. johnsonii* development which was almost comparable to acidification levels after yeast extract addition during a 24 hour fermentation. A final pH of 4.1 was measured after amino acids supplementation, but the cell count was still not satisfactory. The cell count when a 10% skim milk with 19 amino acids added increased from $1.0 \times 10^7$ CFU/ml to $40 \times 10^7$ CFU/ml, which is a factor of 40 increase but is less than the factor of 300 increase observed with 10% skim milk and yeast extract.

In order to determine those amino acids having an essential role for *L. johnsonii* growth in milk, the "omission technique" (Reiter, B. & Oram, J. D, I. Dairy Res, 29 (1962), 63–77) was applied by culturing the strain ATCC $33200^T$ in skim milk, adding four ribonucleosides and ferrous sulphate (positive control), supplemented with the mixture of 19 amino acids described above deprived of one particular component at each given time. Rapid Analysis of Bacterial Impedance Technique (RABIT) allowed the identification of four amino acids (cysteine, alanine, serine and isoleucine) that showed excellent results.

The latter three—alanine, serine and isoleucine—were thought to be stimulants for the tested strain when exogenously added to the milk. The strongest role, among the identified amino acids, was attributed to cysteine. The absence of cysteine or cystine in milk may negatively affect bacterial development. The role of —SH groups seems not completely replaceable by anaerobiosis. The absence of oxygen realized by anaerobic incubation of the *L. johnsonii* cultures did not match the growth results obtained when cysteine was supplemented to skim or whole fat milk.

The pH measurement revealed a value of pH 4.3 in absence of cysteine under anaerobic conditions against a pH of 3.9 obtained in the presence of this compound under aerobic conditions. However, the removal of cysteine resulted in a more significant loss of the viable cell numbers in an aerobic rather than an anaerobic environment. When *L. johnsonii* was cultured under aerobic conditions, a solution of thioglycollic acid (final concentration 0.5% v/v) revealed its ability to replace cysteine, resulting in high cell counts of more than $100 \times 10^7$ CFU/ml.

In spite of the stimulatory actions due to the four cited amino acids (cysteine, alanine, serine and isoleucine), an unexpected negative effect was observed for all other 15 amino acids.

The results of a series of fermentation tests to compare of the effectiveness of free bases, ribonucleosides, and deoxyribonucleosides are shown in Table 2. The final pH after 24 hours incubation at 37° C. of *L. johnsonii* Lal (NCC 533) in 10% skim milk (initial pH 6.8) supplemented with 0.1 g/l each of free bases (adenine, cytosine, guanine, uracil and thymine), or ribonucleosides (adenosine, cytidine, guanosine, and uridine) or deoxyribonucleosides (2'-deoxyadenosine, 2'-deoxyguanosine, 2'-deoxycytidine, 2'-deoxyuridine, and thymidine) are shown in Table 2. This data showed ribonucleosides were more effective in an anaerobic environment, while deoxyribonucleosides were more effective in an aerobic environment for this particular strain of cells. However, none of these fermentations reached the low pH of about 4 reached after fermenting the base supplemented with yeast extract.

TABLE 2

| 10% skim milk and Additives* | Aerobiosis | Anaerobiosis |
| --- | --- | --- |
| Freebases | 5.9 | 5.8 |
| Ribonucleosides | 6.3 | 5.6 |
| Deoxyribonucleosides | 5.8 | 5.9 |

Examples were performed with UHT whole milk gave similar results.

Results of incubation tests with a preferred combination of supplemental additives are shown in Table 3. This Table 3 contains the final pH after 24 hours incubation at 37° C. of *L. johnsonii* La I (NCC 533) and other *L. johnsonii* strains in 10% skim milk, under aerobic and anaerobic incubation conditions, and whole fat UHT milk, each supplemented with four ribonucleosides, four amino acids and ferrous sulphate. Similar results were obtained for other strains.

This data, compared to the growth data of milk without supplements and with yeast extract supplements that were shown in Table 1, shows the improved growth patterns across a wide variety of *L. johnsonii* strains. Un-supplemented 10% skim milk inoculated with *L. johnsonii* La 1 (NCC 533) reached a pH of 6.0 after 24 hours of aerobic incubation. The yeast extract supplemented 10% skim milk inoculated with *L. johnsonii* La 1 (NCC 533) reached a pH of 3.9 after 24 hours of aerobic incubation. The ribonucleosides, four amino acids and ferrous sulphate supplemented 10% skim milk inoculated with *L. johnsonii* La 1 (NCC 533) reached a pH of 4.0 after 24 hours of aerobic incubation.

TABLE 3

|  | NCC 533 | ATCC 33200 | DSM 20553 | ATCC 332 | ATCC 11506 | DSM 33199 |
| --- | --- | --- | --- | --- | --- | --- |
| Aerobiosis | final pH | final pH | final pH | final pH | final pH | final pH |
| 10% skim milk | 4.0 | 5.4 | 4.2 | 5.1 | 5.3 | 4.5 |
| whole fat UHT milk | 3.9 | 5.5 | 4.8 | 6.2 | 5.4 | 4.5 |
| Anaerobiosis |  |  |  |  |  |  |
| 10% skim milk | 4.2 | N.D. | N.D. | N.D. | N.D. | N.D. |

N.D. means not determined.

We claim:

1. A medium for growing Lactobacilli comprising: a milk-derived base; and an additive system that comprises at least four free amino acids, at least two nucleosides, and iron, in amounts sufficient in combination to promote growth of lactobacilli in the medium.

2. The medium according to claim 1, wherein the nucleosides are ribonucleosides, each added in the range of from about 10 to about 500 milligrams per liter of the medium.

3. The medium according to claim 1, wherein the nucleosides are selected from the group consisting of adenosine, guanosine, cytidine, and uridine, and wherein the at least four free amino acids added comprise cysteine.

4. The medium according to claim 3, wherein the nucleosides consist essentially of a combination of adenosine and guanosine or cytidine and uridine; or a mixture of the combination.

5. The medium according to claim 1, wherein the amount of iron added is in the range of about 10 to 200 milligrams of iron per liter of the medium.

6. The medium according to claim 1, wherein the at least four free amino acids added comprise cysteine, alanine, serine and isoleucine, each in an amount ranging from about 10 to about 200 milligrams per liter of the medium.

7. The medium according to claim 1, further comprising a compound that provides antioxidant or reducing activity.

8. The medium according to claim 7, wherein the compound that provides antioxidant or reducing activity is selected from the group consisting of cysteine, thioglycollic acid, ascorbic acid and mixtures thereof.

9. The medium according to claim 1, further comprising added magnesium and aspartic acid.

10. The medium according to claim 9, wherein the at least four free amino acids added comprise cysteine, alanine, serine and isoleucine, each in an amount ranging from about 10 to about 200 milligrams per liter of the medium; wherein the nucleosides added are each in the range of from about 10 to about 500 milligrams per liter of the medium; and wherein the iron added is in the range of about 10 to about 200 milligrams per liter of the medium.

11. The medium according to claim 1, wherein the milk-derived base comprises whole milk, partially de-fatted milk, skim milk or ultra-high temperature pasteurized milk, whether the milk derived base is prepared from a natural source or from dried milk powder by addition of water.

12. The medium according to claim 1, wherein for each nucleoside said nucleosides comprise a combination of adenosine and guanosine, or cytidine and uridine in an amount of 0.1 g/l each, and wherein said at least four free amino acids comprise alanine, serine, isoleucine and cysteine in an amount of 0.05 g/l each; and wherein said from is $FeSO_4$ in an amount of 0.1 g/l.

13. A medium for growing Lactobacilli comprising: a milk-derived base; and an additive system that comprises at least four free amino acids, at least two nucleosides selected from the group consisting of adenosine, guanosine, cytidine, and uridine each added in the range of from about 10 to about 500 milligrams per liter of the medium, and iron in the range of about 10 to 200 milligrams of iron per liter of the medium to promote growth of lactobacilli in the medium.

14. The medium according to claim 13, wherein the at least four free amino acids added comprise cysteine, alanine, serine and isoleucine, each in an amount ranging from about 10 to about 200 milligrams per liter of the medium.

15. The medium according to claim 14, further comprising a compound that provides antioxidant or reducing activity selected from the group consisting of cysteine, thioglycollic acid, ascorbic acid-and mixtures thereof.

16. The medium according to claim 15, further comprising added magnesium and aspartic acid.

* * * * *

UNITED STATES PATENT AND TRADEMARK OFFICE
CERTIFICATE OF CORRECTION

PATENT NO.    : 6,521,443 B1
DATED         : February 18, 2003
INVENTOR(S)   : Zink et al.

It is certified that error appears in the above-identified patent and that said Letters Patent is hereby corrected as shown below:

<u>Column 8,</u>
Line 31, change "whether the milk derived base" to -- wherein the milk-derived base --;
Lines 33-34, delete "for each nucleoside";
Line 36, delete "each," and insert -- for each nucleside, --;
Line 38, delete "from" and insert -- iron --; and
Line 55, change "acid-and" to -- acid and --.

Signed and Sealed this

Twenty-fourth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,521,443 B1
DATED : February 18, 2003
INVENTOR(S) : Zink et al.

It is certified that error appears in the above-identified patent and that said Letters Patent is hereby corrected as shown below:

Column 8,
Line 31, change "whether the milk derived base" to -- wherein the milk-derived base --;
Lines 33-34, delete "for each nucleoside";
Line 36, delete "each," and insert -- for each nucleoside, --;
Line 38, delete "from" and insert -- iron --; and
Line 55, change "acid-and" to -- acid and --.

This certificate supersedes Certificate of Correction issued June 24, 2003.

Signed and Sealed this

Nineteenth Day of August, 2003

JAMES E. ROGAN
*Director of the United States Patent and Trademark Office*